(12) United States Patent
Nesbitt (10) Patent No.: US 8,048,471 B2
(45) Date of Patent: *Nov. 1, 2011

(54) MARKED PRECOATED MEDICAL DEVICE AND METHOD OF MANUFACTURING SAME

(75) Inventor: Bruce Nesbitt, Chicago, IL (US)

(73) Assignee: Innovatech, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/962,326

(22) Filed: Dec. 21, 2007

(65) Prior Publication Data

US 2009/0162530 A1    Jun. 25, 2009

(51) Int. Cl.
*C08J 7/18* (2006.01)
*A61L 33/00* (2006.01)
*A61L 24/00* (2006.01)

(52) U.S. Cl. ......... 427/2.1; 427/557; 427/558; 427/559; 427/560; 523/113

(58) Field of Classification Search .................. 427/2.1, 427/2.12, 2.3, 532, 557–560; 523/113, 334; 204/487; 604/265
See application file for complete search history.

(56) References Cited

U.S. PATENT DOCUMENTS

| | | |
|---|---|---|
| 1,617,102 A | 2/1927 | Cohn |
| 1,772,846 A | 8/1930 | Spolidoro |
| 2,049,769 A | 8/1936 | Gray |
| 2,241,282 A | 5/1941 | Wackerle |
| 2,241,283 A | 5/1941 | Wackerle |
| 2,735,258 A | 2/1956 | Crandall |
| 2,861,417 A | 11/1958 | Crandall |
| 2,892,374 A | 6/1959 | Ralls, Jr. |
| 3,085,912 A | 4/1963 | Friese |
| 3,099,595 A | 7/1963 | Allbaugh |
| 3,120,144 A | 2/1964 | Bayer |
| 3,706,883 A | 12/1972 | McIntyre |
| 3,812,842 A | 5/1974 | Rodriguez |
| 3,857,934 A | 12/1974 | Bernstein et al. |
| 4,003,369 A | 1/1977 | Heilman et al. |
| 4,008,351 A | 2/1977 | Inoue et al. |
| 4,016,714 A | 4/1977 | Crandall, Jr. |
| 4,080,706 A | 3/1978 | Heilman et al. |
| 4,336,087 A | 6/1982 | Martuch et al. |
| 4,377,620 A | 3/1983 | Alexander |
| 4,382,358 A | 5/1983 | Tappe et al. |
| 4,539,228 A | 9/1985 | Lazarus |
| 4,540,628 A | 9/1985 | Oberdeck et al. |
| 4,570,170 A | 2/1986 | Hiraishi et al. |
| 4,577,637 A | 3/1986 | Mueller, Jr. |
| 4,645,491 A | 2/1987 | Evans |
| 4,724,846 A | 2/1988 | Evans, III |
| 4,779,628 A | 10/1988 | Machek |
| 4,796,637 A | 1/1989 | Mascuch et al. |
| 4,799,496 A | 1/1989 | Hargreaves et al. |
| 4,846,193 A | 7/1989 | Tremulis et al. |
| 4,854,330 A | 8/1989 | Evans, III et al. |
| 4,875,489 A | 10/1989 | Messner et al. |
| 4,895,168 A | 1/1990 | Machek |
| 4,922,923 A | 5/1990 | Gambale et al. |
| 4,951,686 A | 8/1990 | Herlitze |
| 4,966,163 A | 10/1990 | Kraus et al. |
| 5,034,005 A | 7/1991 | Appling |
| 5,038,458 A | 8/1991 | Wagoner et al. |
| 5,063,935 A | 11/1991 | Gambale |
| 5,084,022 A | 1/1992 | Claude |
| 5,091,284 A | 2/1992 | Bradfield |
| 5,107,852 A | 4/1992 | Davidson et al. |
| 5,114,401 A | 5/1992 | Stuart et al. |
| 5,117,838 A | 6/1992 | Palmer et al. |
| 5,117,839 A | 6/1992 | Dance |
| 5,144,959 A | 9/1992 | Gambale et al. |
| 5,149,965 A | 9/1992 | Marks |
| 5,154,705 A | 10/1992 | Fleischhacker et al. |
| 5,165,013 A | 11/1992 | Faris |
| 5,165,421 A | 11/1992 | Fleischhacker et al. |
| 5,174,302 A | 12/1992 | Palmer |

(Continued)

FOREIGN PATENT DOCUMENTS

EP    0 321 091    6/1989

(Continued)

OTHER PUBLICATIONS

International Search Report for Application No. PCT/US08/83604, mailed on Jan. 21, 2009.

(Continued)

*Primary Examiner* — Vasu Jagannathan
*Assistant Examiner* — Hannah Pak
(74) *Attorney, Agent, or Firm* — K&L Gates LLP (57) ABSTRACT

A medical device, such as a medical wire, which includes a coating applied to the surface of the medical wire. The coating includes a base layer bonded to the surface of the medical wire and an at least partially transparent low-friction top coat applied to the base layer. The base layer includes heat activated pigments that change color when heated above a color shifting temperature. In one embodiment, the color of the pigment in one area contrasts with the color of the pigment in an adjacent area without otherwise affecting the low-friction surface of the coating. The areas of different color created in locations along the length of the low-friction coated medical wire form markings which enable a surgeon to determine the length of the medical wire inserted into a body by observing the markings on the portion of the marked medical wire located exterior to the body.

32 Claims, 5 Drawing Sheets

U.S. PATENT DOCUMENTS

| | | | |
|---|---|---|---|
| 5,203,777 A | 4/1993 | Lee |
| 5,211,636 A | 5/1993 | Mische |
| 5,234,002 A | 8/1993 | Chan |
| 5,241,970 A | 9/1993 | Johlin, Jr. et al. |
| 5,243,996 A | 9/1993 | Hall |
| 5,260,985 A | 11/1993 | Mosby |
| 5,265,622 A | 11/1993 | Barbere |
| 5,267,955 A | 12/1993 | Hanson |
| 5,271,415 A | 12/1993 | Foerster et al. |
| 5,273,526 A | 12/1993 | Dance et al. |
| 5,279,546 A | 1/1994 | Mische et al. |
| 5,279,573 A | 1/1994 | Klosterman |
| 5,282,478 A | 2/1994 | Fleischhaker, Jr. et al. |
| 5,300,048 A | 4/1994 | Drewes, Jr. et al. |
| 5,345,945 A | 9/1994 | Hodgson et al. |
| 5,353,808 A | 10/1994 | Viera |
| 5,360,403 A | 11/1994 | Mische |
| 5,373,619 A | 12/1994 | Fleischhacker et al. |
| 5,376,083 A | 12/1994 | Mische |
| 5,379,779 A | 1/1995 | Rowland et al. |
| 5,409,004 A | 4/1995 | Sloan |
| 5,433,200 A | 7/1995 | Fleischhacker, Jr. |
| 5,443,081 A | 8/1995 | Klosterman |
| D363,544 S | 10/1995 | Rowland et al. |
| D363,776 S | 10/1995 | Rowland et al. |
| 5,479,938 A | 1/1996 | Weier |
| 5,497,783 A | 3/1996 | Urick et al. |
| 5,497,786 A | 3/1996 | Urick |
| 5,498,250 A | 3/1996 | Prather |
| 5,546,958 A | 8/1996 | Thorud et al. |
| 5,551,444 A | 9/1996 | Finlayson |
| 5,559,297 A | 9/1996 | Yoshikawa et al. |
| 5,606,981 A | 3/1997 | Tartacower et al. |
| 5,610,348 A | 3/1997 | Aladin et al. |
| 5,634,897 A | 6/1997 | Dance et al. |
| 5,640,970 A | 6/1997 | Arenas |
| 5,665,103 A | 9/1997 | Lafontaine et al. |
| 5,669,878 A | 9/1997 | Dickinson et al. |
| 5,724,989 A | 3/1998 | Dobson |
| 5,728,042 A | 3/1998 | Schwager |
| H1715 H | 4/1998 | Longeat |
| 5,740,473 A | 4/1998 | Tanaka et al. |
| 5,741,267 A | 4/1998 | Jorneus et al. |
| 5,759,174 A | 6/1998 | Fischell et al. |
| 5,782,811 A | 7/1998 | Samson et al. |
| 5,801,319 A | 9/1998 | Hebestreit |
| 5,804,633 A | 9/1998 | Loftin et al. |
| 5,807,279 A | 9/1998 | Viera |
| 5,830,155 A | 11/1998 | Frechette et al. |
| 5,836,892 A | 11/1998 | Lorenzo |
| 5,876,783 A | 3/1999 | Dobson |
| 5,883,319 A | 3/1999 | Hebestreit |
| 5,885,227 A | 3/1999 | Finlayson |
| 5,897,819 A | 4/1999 | Miyata et al. |
| 5,898,117 A | 4/1999 | Ishida |
| 5,907,113 A | 5/1999 | Hebestreit |
| 5,908,413 A | 6/1999 | Lange et al. |
| 5,919,126 A | 7/1999 | Armini |
| 5,919,170 A | 7/1999 | Woessner |
| 5,941,706 A | 8/1999 | Ura |
| 5,948,489 A | 9/1999 | Hopkins |
| 5,970,119 A | 10/1999 | Hofmann |
| 5,984,877 A | 11/1999 | Fleischhacker, Jr. |
| 6,036,682 A | 3/2000 | Lange et al. |
| 6,042,605 A | 3/2000 | Martin et al. |
| 6,048,620 A | 4/2000 | Zhong |
| 6,050,958 A | 4/2000 | Dickinson et al. |
| 6,083,167 A | 7/2000 | Fox et al. |
| 6,093,157 A | 7/2000 | Chandrasekaran |
| 6,093,678 A | 7/2000 | Hamada et al. |
| 6,113,576 A | 9/2000 | Dance et al. |
| 6,139,540 A | 10/2000 | Rost et al. |
| 6,140,267 A | 10/2000 | Gundjian |
| 6,143,013 A | 11/2000 | Samson et al. |
| 6,168,570 B1 | 1/2001 | Ferrera |
| 6,179,788 B1 | 1/2001 | Sullivan |
| 6,193,706 B1 | 2/2001 | Thorud et al. |
| 6,211,450 B1 | 4/2001 | Ishida |
| 6,238,847 B1 | 5/2001 | Axtell, III et al. |
| 6,248,942 B1 | 6/2001 | Hebestreit et al. |
| 6,273,858 B1 | 8/2001 | Fox et al. |
| 6,277,108 B1 | 8/2001 | Mcbroom et al. |
| 6,306,105 B1 | 10/2001 | Rooney et al. |
| 6,315,790 B1 | 11/2001 | Gerberding et al. |
| 6,340,368 B1 | 1/2002 | Verbeck |
| 6,348,646 B1 | 2/2002 | Parker et al. |
| 6,361,557 B1 | 3/2002 | Gittings et al. |
| 6,370,304 B1 | 4/2002 | Mills et al. |
| 6,387,060 B1 | 5/2002 | Jalisi |
| 6,425,927 B1 | 7/2002 | Haupt-Stephan et al. |
| 6,428,512 B1 | 8/2002 | Anderson et al. |
| 6,468,079 B1 | 10/2002 | Fischer et al. |
| 6,475,169 B2 | 11/2002 | Ferrera |
| 6,491,646 B1 | 12/2002 | Blackledge |
| 6,501,827 B1 | 12/2002 | Takasawa |
| 6,501,992 B1 | 12/2002 | Belden et al. |
| 6,503,310 B1 | 1/2003 | Sullivan |
| 6,520,923 B1 | 2/2003 | Jalisi |
| 6,520,934 B1 | 2/2003 | Lee et al. |
| 6,528,709 B2 | 3/2003 | Hebestreit et al. |
| 6,540,721 B1 | 4/2003 | Voyles et al. |
| 6,554,942 B2 | 4/2003 | Solar et al. |
| 6,605,049 B1 | 8/2003 | Wagner et al. |
| 6,612,998 B2 | 9/2003 | Gosiengfiao et al. |
| 6,613,002 B1 | 9/2003 | Clark et al. |
| 6,617,515 B1 | 9/2003 | Yeung |
| 6,619,778 B2 | 9/2003 | Igarashi |
| 6,620,114 B2 | 9/2003 | Vrba et al. |
| 6,623,504 B2 | 9/2003 | Vrba et al. |
| 6,626,869 B1 | 9/2003 | Bint |
| 6,636,758 B2 | 10/2003 | Sanchez et al. |
| 6,638,589 B2 | 10/2003 | Jarvenkyla |
| 6,652,568 B1 | 11/2003 | Becker et al. |
| 6,652,579 B1 | 11/2003 | Cox et al. |
| 6,673,025 B1 | 1/2004 | Richardson et al. |
| 6,679,853 B1 | 1/2004 | Jalisi |
| 6,680,121 B2 | 1/2004 | Sakoske et al. |
| 6,733,503 B2 | 5/2004 | Layrolle et al. |
| 6,758,857 B2 | 7/2004 | Cioanta et al. |
| 6,765,136 B2 | 7/2004 | Van Pamel |
| D496,728 S | 9/2004 | Holsinger |
| 6,811,805 B2 | 11/2004 | Gilliard et al. |
| 6,811,958 B2 | 11/2004 | Iwani et al. |
| 6,835,454 B1 | 12/2004 | Randa et al. |
| 6,855,161 B2 | 2/2005 | Boylan et al. |
| 6,942,652 B1 | 9/2005 | Pressly, Sr. et al. |
| 6,994,883 B2 | 2/2006 | Layrolle et al. |
| 7,022,086 B2 | 4/2006 | Her |
| 7,033,325 B1 | 4/2006 | Sullivan |
| 7,147,634 B2 | 12/2006 | Nesbitt |
| 7,150,756 B2 | 12/2006 | Levinson et al. |
| 7,153,277 B2 | 12/2006 | Skujins et al. |
| 7,160,297 B2 | 1/2007 | Nesbitt |
| 7,163,509 B2 | 1/2007 | Abe |
| 7,182,757 B2 | 2/2007 | Miyata et al. |
| 7,217,876 B2 | 5/2007 | Allen et al. |
| 7,241,406 B2 | 7/2007 | Solar et al. |
| 7,255,685 B2 | 8/2007 | Pressly, Sr. et al. |
| 7,261,925 B2 | 8/2007 | Nesbitt |
| 7,278,973 B2 | 10/2007 | Iwami et al. |
| 7,288,091 B2 | 10/2007 | Nesbitt |
| 7,296,333 B2 | 11/2007 | Jalisi |
| 7,309,235 B2 | 12/2007 | Wilk |
| 7,311,714 B1 | 12/2007 | Wascher |
| 7,390,326 B2 | 6/2008 | Nesbitt |
| 7,399,296 B2 | 7/2008 | Poole et al. |
| 7,408,101 B2 | 8/2008 | Shelton |
| 7,434,437 B2 | 10/2008 | Kato et al. |
| 7,455,646 B2 | 11/2008 | Richardson et al. |
| 7,473,417 B2 | 1/2009 | Zeltinger et al. |
| 7,517,342 B2 | 4/2009 | Scott et al. |
| 7,714,217 B2 | 5/2010 | Nesbitt |
| 2002/0082681 A1 | 6/2002 | Boylan et al. |
| 2002/0136893 A1 | 9/2002 | Schlesinger |
| 2003/0032896 A1 | 2/2003 | Bosley, Jr. et al. |
| 2003/0060731 A1 | 3/2003 | Fleischhacker |
| 2003/0060783 A1 | 3/2003 | Koole et al. |

| | | | |
|---|---|---|---|
| 2003/0060872 A1 | 3/2003 | Gomringer et al. | |
| 2003/0109865 A1 | 6/2003 | Greep et al. | |
| 2003/0120302 A1 | 6/2003 | Minck, Jr. et al. | |
| 2003/0139764 A1 | 7/2003 | Levinson et al. | |
| 2003/0199759 A1 | 10/2003 | Richard | |
| 2003/0203991 A1 | 10/2003 | Schottman et al. | |
| 2003/0216642 A1 | 11/2003 | Pepin et al. | |
| 2004/0044399 A1 | 3/2004 | Ventura | |
| 2004/0122509 A1 | 6/2004 | Brodeur | |
| 2004/0220608 A1 | 11/2004 | D'aquanni et al. | |
| 2004/0253185 A1 | 12/2004 | Herweck et al. | |
| 2004/0267161 A1 | 12/2004 | Osborne et al. | |
| 2005/0003103 A1* | 1/2005 | Krupa | 427/558 |
| 2005/0011332 A1 | 1/2005 | Dronge | |
| 2005/0038500 A1 | 2/2005 | Boylan et al. | |
| 2005/0087520 A1 | 4/2005 | Wang et al. | |
| 2005/0133941 A1 | 6/2005 | Schuhmacher | |
| 2005/0148902 A1 | 7/2005 | Minar et al. | |
| 2005/0154075 A1 | 7/2005 | Siegel | |
| 2005/0165472 A1 | 7/2005 | Glocker | |
| 2005/0187466 A1 | 8/2005 | Glocker et al. | |
| 2005/0261670 A1 | 11/2005 | Weber et al. | |
| 2005/0266170 A1* | 12/2005 | Nesbitt | 427/475 |
| 2005/0288773 A1 | 12/2005 | Glocker et al. | |
| 2006/0036316 A1 | 2/2006 | Zeltinger et al. | |
| 2006/0118612 A1 | 6/2006 | Christoffersen et al. | |
| 2006/0174745 A1 | 8/2006 | D'Addario | |
| 2006/0174746 A1 | 8/2006 | Everly | |
| 2006/0184112 A1 | 8/2006 | Horn et al. | |
| 2006/0211952 A1 | 9/2006 | Kennedy, II | |
| 2006/0257653 A1 | 11/2006 | Tsujimoto et al. | |
| 2006/0259033 A1 | 11/2006 | Nesbitt | |
| 2006/0271135 A1 | 11/2006 | Minar et al. | |
| 2007/0021811 A1 | 1/2007 | D'aquanni et al. | |
| 2007/0093811 A1 | 4/2007 | Nesbitt | |
| 2007/0100279 A1 | 5/2007 | Bates | |
| 2007/0118113 A1 | 5/2007 | Nesbitt | |
| 2007/0207182 A1 | 9/2007 | Weber et al. | |
| 2007/0208373 A1 | 9/2007 | Zaver et al. | |
| 2007/0212547 A1 | 9/2007 | Fredrickson et al. | |
| 2007/0266542 A1 | 11/2007 | Melsheimer | |
| 2008/0008654 A1 | 1/2008 | Clarke et al. | |
| 2008/0027532 A1 | 1/2008 | Boylan et al. | |
| 2008/0032060 A1 | 2/2008 | Nesbitt | |
| 2008/0033373 A1 | 2/2008 | Koole et al. | |
| 2008/0050509 A1 | 2/2008 | Nesbitt | |
| 2008/0108974 A1 | 5/2008 | Yee | |
| 2008/0288056 A1 | 11/2008 | Simpson et al. | |
| 2009/0158912 A1* | 6/2009 | Nesbitt | 84/297 S |
| 2009/0162531 A1* | 6/2009 | Nesbitt | 427/2.12 |
| 2009/0181156 A1* | 7/2009 | Nesbitt et al. | 427/2.1 |
| 2009/0211909 A1* | 8/2009 | Nesbitt | 204/487 |

FOREIGN PATENT DOCUMENTS

| | | |
|---|---|---|
| EP | 0 624 380 | 11/1994 |
| EP | 0 771 572 | 5/1997 |
| EP | 0 832 664 | 4/1998 |
| EP | 0 987 042 | 3/2000 |
| EP | 0 749 334 | 6/2000 |
| EP | 1 025 811 | 8/2000 |
| EP | 1 062 965 | 12/2000 |
| EP | 0 833 676 | 9/2003 |
| EP | 1 433 438 | 6/2004 |
| WO | WO/95/14501 | 6/1995 |
| WO | WO/01/45592 | 6/2001 |
| WO | WO/02/47549 | 6/2002 |
| WO | WO/2004/033016 | 4/2004 |
| WO | WO 2004/049970 | 6/2004 |
| WO | WO/2004/110519 | 12/2004 |
| WO | WO/2005/094486 | 10/2005 |
| WO | WO/2005/122961 | 12/2005 |
| WO | WO/2006/002199 | 1/2006 |
| WO | WO 2006/006971 | 1/2006 |
| WO | WO 2006/019983 | 2/2006 |
| WO | WO/2007/100556 | 9/2007 |
| WO | WO/2008/097359 | 8/2008 |

OTHER PUBLICATIONS

International Search Report and the Written Opinion of the International Searching Authority, dated Jun. 22, 2009, for PCT/US09/42697.
Plastics Laser Marking in the Aerospace Industry, Article, published by The Sabreen Group, Inc., [online] [retrieved from the Internet Nov. 26, 2007] <URL:www.plasticslasermarking.com/laser_marking_aerospace.htm>.
Marking Processes for Use in Harsh Environments, Article, published by The Sabreen Group, Inc., [online] [retrieved from the Internet Nov. 26, 2007] <URL:www.plasticslasermarking.com/laser_marking_harsh_environments.htm>.
Advancements in Laser Marking of Plastics, Article, published by The Sabreen Group, Inc., prior to 2007.
Total Solutions for High Contrast Laser Marking of Plastics and Metals Substrates, Article, published by the Sabreen Group, Inc., [online] [retrieved from the Internet Nov. 26, 2007] <URL:www.plasticslasermarking.com/laser_marking.htm>.
Acetal (POM) Engineering Property Data, Article, published by Material Property Data, [online] [retrieved from the Internet Nov. 26, 2007] <URL:www.matweb.com/reference/acetalpolymer.aspx>.
Sabreen, Scott R., New Technologies for High-Speed Color Laser Marking of Plastics, Article, published by Plastics Decorating Magazine, Oct./Nov. 2004.
Total solutions for High Contrast & Color Laser Marking, Article, Published by The Sabreen Group, Inc., [online] [retrieved from the Internet Nov. 26, 2007] <URL:www.plasticslasermarking.com/metals_laser_marking.htm>.
Office Action of U.S. Appl. No. 12/211,630 dated Aug. 18, 2009.
UV40 Dual Care Acrylated Urethane Coating Technical Data Sheet: Chase Specialty Coatings, pp. 1-3, Jul. 2007.
Nagaoka et al., "Low Friction Hydrophillic Surface for medical Device", BioMaterials, Aug. 11, 1990, pp. 419-424.
ClearClad: "Electrophoretic Coating", pp. 1-4, 1996-2002.
Dec. 23, 2009 Office Action for U.S. Appl. No. 12/402,218.
International Preliminary Report on Patentability, dated Jan. 11, 2011 for PCT/US2009/042697.
Aug. 5, 2010 Office Action for U.S. Appl. No. 12/766,426.

* cited by examiner

MARKED PRECOATED MEDICAL DEVICE AND METHOD OF MANUFACTURING SAME

This application is related to the following commonly-owned co-pending patent applications: "MARKED PRECOATED MEDICAL DEVICE AND METHOD OF MANUFACTURING SAME," Ser. No. 12/171,847, "MARKED PRECOATED MEDICAL DEVICE AND METHOD OF MANUFACTURING SAME," Ser. No. 12/367,929, "MARKED PRECOATED MEDICAL DEVICE AND METHOD OF MANUFACTURING SAME," Ser. No. 12/402,218, and "MARKED PRECOATED STRINGS AND METHOD OF MANUFACTURING SAME," Ser. No. 12/211,630.

BACKGROUND

Medical devices such as wires, guide wires, probes, mandrels, needles, cannulas, and other medical devices are commonly inserted into humans or animals for therapeutic and diagnostic medical procedures. Often, surgeons or other medical professionals must be able to determine the specific distance that a medical device is inserted into a body. The accurate placement of the medical device is often critical to the procedure. If a medical device is inserted too far into a patient, it could tear, puncture, or otherwise cause damage to internal bodily tissues, vessels, and other organs, which could be harmful or potentially fatal to the patient. Alternatively, if not inserted far enough, the procedure may not be successfully performed. Accordingly, certain medical devices are marked with visual indicia at measured intervals along the length of the device to indicate the length of the medical device inserted into a patient.

Additionally, many medical devices are coated with one or more low friction materials such as polytetrafluoroethylene (PTFE). Low friction coatings reduce the amount of friction between the medical device and bodily tissues, catheters, or other surfaces. Without low friction coatings, certain medical devices are more likely to "stick" to tissues, catheters, or other surfaces during insertion or extraction. If a medical device sticks to other surfaces as it is inserted into a body, a surgeon or other medical professional must apply a greater insertion force to the medical device to reinitiate movement. Once movement is reinitiated, the opposing force immediately decreases so that the medical device is caused to quickly accelerate into the body. Such extreme movements increase the risk of scraping, rubbing, tearing, puncturing, or otherwise damaging a patient's internal tissues due to misplacing the end of the device in the patient. Low friction coatings are less likely to stick to other surfaces and therefore give surgeons or other medical professionals more control or modulate over the insertion speed and depth, which reduces the risk of damage to the patient, thus reducing the "slip-stick" phenomena. Additionally, low friction coatings generally have smooth surfaces that will not scrape, irritate, or snag tissues, vessels or arteries. However, there are very limited methods for marking such devices with low friction coatings.

One known method of marking low friction coated medical devices is to grind, ablate or acid remove the low friction coating to expose the surface of the medical device so that the contrast between the color of the low friction coating and the base metal or surface of the medical device can serve as visual indicia. Ablation is typically achieved by using corrosive chemicals or laser beams, or grinding or grit blasting to selectively remove the coating from the medical device. Such ablation or grinding methods remove the entire coating from the surface of the device, which creates grooves or valleys in the surface of the low-friction or other coating. The shoulders of these grooves or valleys can have sharp edges, particularly when laser beams, grinding, or other similar techniques are used to remove the coating. The resulting sharp edges can scrape bodily tissues, snag vessels or arteries of the patient, or otherwise cause damage and/or trauma to the patient. When inserting medical devices into delicate areas such as the brain and heart, damage caused by the sharp shoulders of the grooves or valleys can be harmful and potentially fatal for the patient. Even if the shoulders are shaped to reduce or eliminate sharp edges, this method of marking low friction coated medical devices still removes the benefits of the low friction coating and exposes the raw, unprotected surface of the medical device, particularly when a wire device changes directions or goes around a turn in a vessel, vein or artery. As described above, the exposed surface of the medical device is more likely to stick to bodily tissues and other surfaces, potentially harming the patient. Additionally, this method of marking low friction coated medical devices creates different diameters along the length of the medical device which can also increase the required insertion force and decrease the control a surgeon or other medical professional can exercise over the speed and depth of an insertion. Therefore, the above method of marking low friction coated medical devices adversely affects the function of the coated medical device and can increase the risk of injury to a patient.

Another known method of marking low friction coated medical devices is to print ink on the surface of the coating. However, low friction coatings resist bonding with inks, and inks printed on low friction coatings may peel off and be left inside the patient's body, which may harm the patient. Ink may also rub or peel off before or during use of the medical device, thus destroying the usefulness of the markings, and increasing the risk that the medical device will be inserted either too deep, or not deep enough (and harm the patient and/or render the medical procedure ineffective). Furthermore, many medical devices have small diameters such that even thin layers of ink can significantly increase the diameter of the device, which, as previously described, is undesirable.

Marking low friction coated medical guide wires poses additional problems. Medical guide wires are generally shaped like coiled springs, having an elongated strand of medical wire helically wound such that adjacent turns of the wire are in contact with each other. Known methods of marking low friction coated medical guide wires, such as grinding or ablating the coating to expose the surface of the medical guide wire each have the disadvantages of either increasing or decreasing the diameter of the medical guide wire and/or removing the low friction coating, which is undesirable. Removal of the coating by mechanical processes such as by grinding or using abrasives could possibly weaken the thin wire that forms the coils of the medical guide wire. Laser ablation does not harm the wire, however it removes the low friction coating which is undesirable. Additionally, despite repeated rinsing, material removed from the coating can get caught between the turns or adjacent segments of the medical wire and can be deposited in a patient's body during a medical procedure, which could be potentially fatal for the patient. Furthermore, marking the coated medical guide wire with paint is not effective because paint will easily crack and delaminate between adjacent turns of the medical guide wire and the paint could be deposited in a patient's body, which could also be harmful and potentially fatal for the patient.

One known method of forming a low-friction coating on a medical device includes applying an aqueous PTFE solution to the surface of a medical device. The solution includes particles of a low friction material such as PTFE, an acid such as chromic acid, a pigment, wetting agents, other ingredients, and water. The solution is cured at a high temperature such as 750° F. (399° C.) to cure the coating. The pigments used in this method are generally stable at temperatures exceeding the cure temperature so that they do not shift color during the curing process. Although the pigments used in this method generally will shift color at temperatures above the cure temperature, when heated to such temperatures the low friction character of the PTFE coating permanently degrades and the bonds between the low friction coating and the medical device weaken, which destroys the coating adhesion and utility of the low friction coating.

Accordingly, a need exists for improved markings on medical devices, and specifically medical wires or tube type devices with low friction coatings. Such a need exists for medical devices with markings that do not significantly increase or decrease the diameter of the medical device, or significantly adversely affect the function of the low friction coating.

SUMMARY

The present disclosure relates in general to medical devices, and specifically to medical devices having low-friction (including low friction, low surface energy and/or non-stick) coatings having visible markings, and a method for manufacturing the same.

In one embodiment, the medical device, such as a medical wire, includes a coating applied to the surface of the medical device. The coating includes a base layer bonded to the surface of the medical device and an at least partially low-friction top coat on the surface of the coating. The base layer includes pigments that change to a different, contrasting color when heated above a discoloration or color shifting temperature, or are otherwise stimulated by suitable stimulants. In one embodiment, the color of the pigment in one area contrasts with the color of the pigment in an adjacent area without otherwise affecting, degrading, deteriorating, compromising or changing the chemical composition of the low-friction coating and/or significantly affecting, degrading, deteriorating, compromising or changing one or more characteristics, functions, or properties of the low-friction coating. The areas of different color created in locations along the length of the low-friction coated medical device form markings which enable a surgeon or other medical professional to determine the length of the medical device inserted into a body by observing the markings on the portion of the device located exterior to the body.

In one embodiment, a coating is applied to the surface of a medical device, such as a medical wire. The coating includes a binder, at least one heat-sensitive pigment, and particles of a low-friction material such as PTFE. The medical device and the applied coating are then heated above a designated temperature, such as 500° F. (260° C.) to cure the coating. The binder and pigment used in this method are generally stable at the cure temperature, but one or both will discolor or shift color at temperatures above a specific temperature greater than 500° F. (260° C.). During the initial curing process, the low-friction particles soften and at least some of the low-friction material migrates or flows to the surface of the coating. At or near the surface of the coating, the low-friction material fuses or glazes over the base layer to create a smooth, substantially continuous top coat comprised of low-friction material. Also during the curing process, the binder material binds with the surface of the medical device and the heat activated pigment is left interspersed within the binder material. When curing is complete, the medical device includes a base layer including a binder material and a heat activated pigment, and an at least partially transparent top coat substantially comprised of low friction or low surface energy materials. One advantage of this method over the aqueous solution method of applying a coating is that the coating in this method is cured at a lower temperature, which enables the pigment to be formulated to shift color at a lower temperature. The lower color shifting temperature enables the color of the pigment to shift without substantially affecting, degrading, deteriorating, compromising or changing the chemical composition of the low-friction material of the coating and/or affecting, degrading, deteriorating, compromising or changing one or more characteristics, functions, or properties of the low-friction material of the coating. The lower color shifting temperature also enables the color of the pigment to shift without substantially affecting, degrading, deteriorating, compromising or changing one or more characteristics, properties, or functions of the adherence of the coating to the surface of the medical device.

After initially curing of the specific coating on the surface of the medical device, markings in the coating are created by selectively heating portions of the coating, including the heat activated pigment, above a color shifting temperature, or by selectively stimulating portions of the coating by using a suitable external stimulant. The color shifting temperature must be greater than the curing temperature, so that the pigment does not shift or change color during the curing process. The color shifting temperature must also be less than the temperatures at which either the binder material significantly loses its adhesion to the surface of the medical device, or the low-friction material of the coating substantially degrades. That is, if the color shifting temperature is too high, then the low-friction character of the top coat will degrade (nullifying the effectiveness of the low-friction coating), and the binder material will lose adhesion to the surface of the medical device (causing the coating to deteriorate, delaminate or peel off) before the pigment can be heated above the color shifting temperature. A proper color shifting temperature enables areas of different or contrasting color to be created after curing and without adversely affecting the low-friction character of the top coat or the adhesion of the base layer to the surface of the medical device. Therefore, a proper color shifting temperature enables markings to be created on the medical device without adversely affecting the function of the medical device or the coating thereon.

In one embodiment, a first area of the low-friction coating is heated to the color shifting temperature to shift or change the color of the heat activated pigment for a specific distance, such as 3 cm as measured from the distal end, proximal end or from the center of the medical device. In this embodiment, a distance, such as 10 cm, is then measured from the first area to a second area. The second area, such as an area of 3 cm in length, is subsequently heated to the color shifting temperature to shift or change the color of the heat activated pigment. Such heatings to create areas of shifted color, when repeated along the length of the device, result in specific length markings at measured intervals. The markings of such depth or distance marked medical devices enable surgeons or other medical professionals to determine, based on a predetermined pattern known to the device user, the length of the medical device inserted into a patient, whether from the proximal or distal end. Accordingly, the medical device and method disclosed herein provide the advantages of having specific markings that do not significantly increase or decrease the diameter of the medical device, or significantly adversely affect the function of the low-friction coating and further provide a coating over the base material of the medical wire or device.

In one embodiment, a coating is applied to the surface of a medical wire. The medical wire is generally elongated and has a proximal end, a distal end, and at least one surface. The medical wire or device is made of steel, stainless steel, aluminum, Nitinol, titanium, copper, plastic, ceramic, or any other suitable material. The coating applied to the surface of the medical wire includes a binder resin (such as an epoxy, polyimide, polyamide, PTFE or polyarylsulfone), and one or more suitable pigments, such as any suitable heat activated pigment, organic pigment, inorganic pigment, extender pigment, magnetic receptive pigment, and/or laser excitable pigment. The coating also includes particles of a low friction and/or low surface energy material such as PTFE, fluorinated ethylene propylene (FEP), polyethylene (PE) or perfluoroalkoxy (PFA). The coating is applied to the surface of the medical device and is cured by heating the coating to a designated temperature and for a designated period of time to cure the binder resin. During the curing process, particles of the binder resin crosslink, sinter, or form bonds with other particles of the binder resin. The specially formulated binder resin also forms bonds with the surface of the medical device. Also during the curing process, some of the low-friction material migrates or flows to the surface of the coating and fuses together to form a substantially continuous glaze or top coat of low-friction material.

In one embodiment, after the coating is cured, portions of the heat activated pigment are heated above the color shifting temperature. In one embodiment, heat is selectively applied to a portion of the top coat, which subsequently heats the base layer underneath the clear top layer. In one embodiment, infrared or laser heat is applied to the base layer by passing the radiated heat through the at least partially transparent top layer. In one embodiment, the medical device is heated by induction and the base layer is heated by conduction from the medical device.

When the base layer is heated to a temperature above the color shifting temperature, the heat activated pigment changes color from a first color to a second different color. The color of the pigment is shifted in selected locations along the length of the device such that the different colors serve as visual indicia which indicate a designated length of the medical device or a designated position on the medical device. Using a jet of hot air, open flame, or other suitable mechanism or apparatus for applying heat, the color of a small length of the medical wire in a first location is shifted such that the wire has a thin, 2 mm for example, band of different color around its circumference. A distance, such as 10 cm, is then measured from the first location having a different color to a second location along the length of the device. The second location is also selectively heated and caused to shift color such that the wire has a second 2 mm band of a different color. In this manner, repeated locations of shifted color along the length of the device indicate to surgeons or other medical professionals the length of the medical wire that is inserted into a patient.

It should be appreciated that the locations of shifted color can be created in any suitable combination of lengths and patterns to indicate different lengths and locations on the medical device. For example, a single mark of 5 cm indicates a location in the exact center of a guide wire. In another example, a pattern of bands can provide a distance marker from the distal end of a medical device. For example, from the exact center of a guide wire toward the distal end, 5 cm marks are provided as a single mark 10 mm from the centerline, another 2 cm mark is proved at 15 mm from the centerline, two bands of 5 cm spaced by 1 cm are provided at 20 mm from the centerline, another band of 2 cm is provided at 25 mm from the centerline followed by three 5 cm bands at 30 mm from the centerline, and so on to the distal end of the device. In another example, a medical device disclosed herein includes a first shifted color (which runs from a distal end of the medical device to a halfway or middle point of the medical device) and a second, contrasting color (which runs from the proximal end of the medical device to the halfway or middle point of the medical device). Such a configuration provides that a surgeon or medical professional can quickly identify when more than 50% of the medical device is internal to the patient and determine whether a different medical device of a different length should be employed. Such a configuration can also assist the surgeon or medical practitioner in determining the length of a catheter or other device which will subsequently be placed over the guide wire to a specified distance, based on the markings on the exposed guide wire. Another mid-point marking system can be a series of 2, 3, 4 and 5 cm marks preceding a centerline mark of two 5 cm marks spaced apart by 1 cm, which denotes the exact centerline of the device. Such a marking system provides the surgeon a warning with the narrower pattern of marks that the centerline is being approached. Accordingly, many marking codes or patterns can be used denoting distance from the distal end of the medical device, the proximal end of the medical device, the centerline of the medical device or any suitable point or location of the medical device required by the medical device manufacturer.

It is therefore an advantage of the medical device and method disclosed herein to provide a marked low-friction coated medical device having markings which do not affect the function or form of the low-friction coating and enable a surgeon or other medical professional to determine the length of a medical device inserted into a patient's body, and to modulate the speed at which the medical device is being inserted or extracted from the patient's body. Such coated medical device provides no dynamic restrictions to any predetermined or required modulation of speed due to the removal or interruption of the low-friction coating to the smooth, low-friction outer surface of the device. The medical device and method disclosed herein further provides a marked medical device with a smooth, continuous low-friction surface with a substantially constant diameter which prevents the medical device from snagging, sticking, tearing, or otherwise damaging vessels, arteries, or other tissues of a patient during insertion, positioning, and extraction of the medical device. The low-friction coating is marked without otherwise affecting, degrading, deteriorating, or changing the chemical composition of, or changing one or more characteristics, functions, or properties of the low-friction coating. The marked low-friction coated medical device disclosed herein enables a surgeon or other medical professional to smoothly, easily, accurately, and safely insert and position the medical device in a patient's body during a medical procedure and know what distance is inserted into the patient's body and what distance remains outside of the patient's body.

Additional features and advantages are described herein, and will be apparent from, the following Detailed Description and the figures.

DETAILED DESCRIPTION

For the purposes of this application only, the medical device is referred to and illustrated as a medical wire or a medical guide wire. However, the medical device disclosed herein is any device that is inserted into a patient in connection with any medical procedure. Such medical devices include, but are not limited to medical wires, medical guide wires, catheters, needles, biopsy tubular sampling devices, soft tissue biopsy devices, hook-type biopsy devices, cannulas, probes and knives. The medical device is constructed from any suitable material, including but not limited to metals such as steel (both high- and low-carbon content), stainless steel, aluminum, titanium, copper, nickel, silver, nitinol, and other metals and metal alloys. Other suitable materials of which a medical device may be constructed include ceramics, rubber, any suitable polymer material and any suitable plastic, including but not limited to nylon, polyetheretherketone (PEEK), polyetherketone (PEK), polyphenylenesulphide (PPS), acrylonitrile-butadiene-styrene (ABS), polycarbonate, epoxy, polyester, and phenolic, or any combination thereof. It should be appreciated that various changes and modifications to the presently preferred embodiments described herein will be apparent to those skilled in the art. Such changes and modifications can be made without departing from the spirit and scope of the present subject matter and without diminishing its intended advantages.

Figure 2:
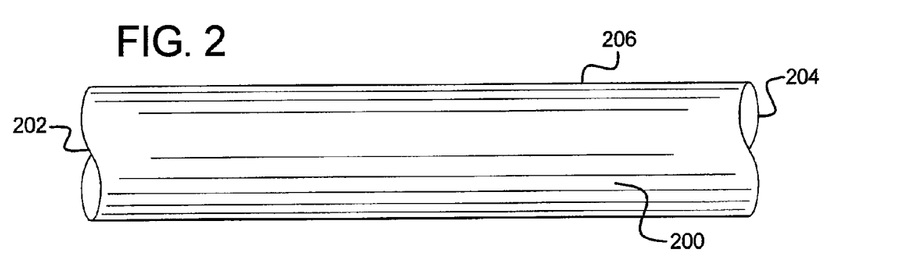
FIG. 2 is a side view of one embodiment of a segment of an uncoated medical device disclosed herein.

In one embodiment, the medical device illustrated in FIG. 2 is an medical wire before having a coating applied thereto. The medical wire 200 is generally elongated and has a proximal end 202, a distal end 204, and an outer surface 206. In one embodiment, the medical device is a medical guide wire, wherein the guide wire includes one or more elongated strands of coated medical wire helically wound such that adjacent turns of the wire are in contact with each other. The resulting medical guide wire is generally shaped like a coiled spring and includes a proximal end and a distal end.

Figure 1:
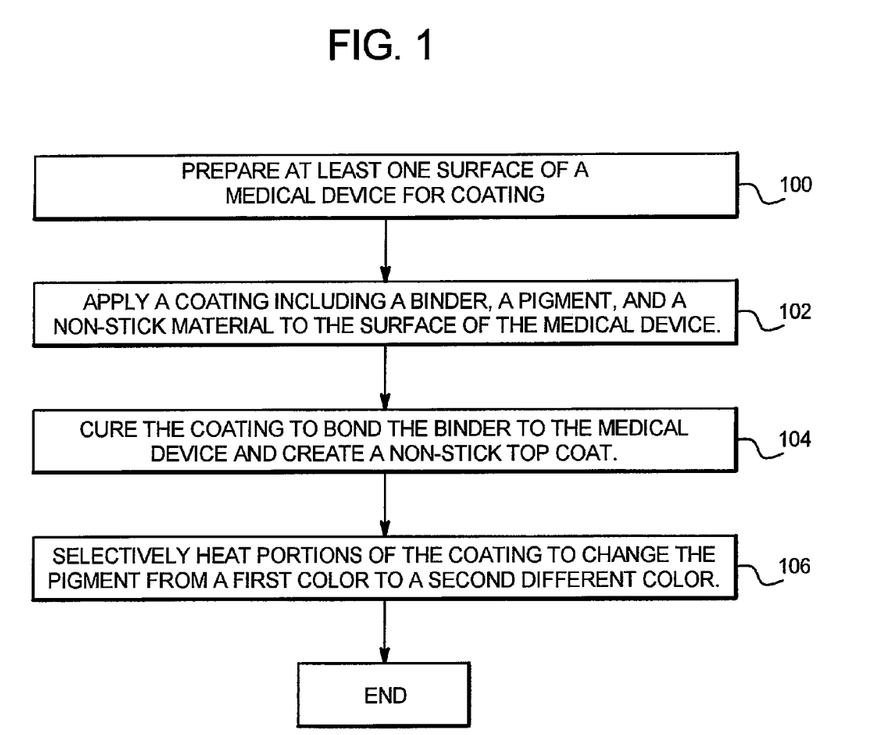
FIG. 1 is a flow chart describing one embodiment of the disclosed method of coating and marking a medical device.

In one embodiment, referring to FIG. 1, before applying a coating to the surface of the medical device, in this case a medical wire, the medical wire is prepared for coating as indicated in block 100 of FIG. 1. In one such embodiment, the medical wire is cleaned with a cleaner to remove impurities which are present on the surface of the medical wire. Impurities such as oils may impede bonding of a coating to the surface of the medical wire, and also may cause damage to a patient if inserted into a patient's body during a medical procedure. The cleaner, such as a solvent, acid solution or alkaline, is manually applied, mechanically applied or ultrasonically applied to the medical wire. In one embodiment, the medical wire is cleaned by condensing a vaporized cleaner on the surface of the medical wire, wherein the cleaner dissolves and washes away the oils on the surface of the medical wire. In another embodiment, grit blasting, tumble blasting, or sandblasting with a medium such as aluminum oxide, garnet, or silicone carbide is used to clean the surface of the medical wire and create a roughened surface which promotes bonding with a coating. In another embodiment, the surface of the medical wire is etched with acid or alkaline to clean and roughen the surface of the medical wire. In another embodiment, the medical wire is cleaned with an ultrasonic cleaner used in combination with a solvent such as acetone or another degreaser. Alternatively, the medical wire is pre-cleaned or the method is performed in a "clean room" where the cleaned part is manufactured and the step is not necessary. In another embodiment, the medical wire is heated to a temperature, depending on the metal alloy or other material of the medical wire, in excess of 700° F. (371° C.) for a period of time sufficient to thermally degrade surface impurities, draw oils and other impurities out of any pores in the surface of the medical wire and create a non-acidic "passivation" of the surface of the medical wire. In another embodiment, the medical wire is cleaned in a batch or bulk cleaning method, thereby cleaning all of the surfaces of the medical wire. In another embodiment, the medical wire is heated before applying a coating to reduce ambient moisture on the surface of the medical wire and improve adhesion of a coating to the medical wire. In another embodiment, the medical wire is cleaned with a grit-blasting system which includes several grit-blasting nozzles cleaning the surface of the medical wire with relatively high velocity particles of an abrasive such as aluminum oxide or silicon carbide. In other embodiments, any combination of the cleaning methods mentioned above are used to improve the cleaning process and promote adhesion of a coating to the medical wire.

Figure 3:
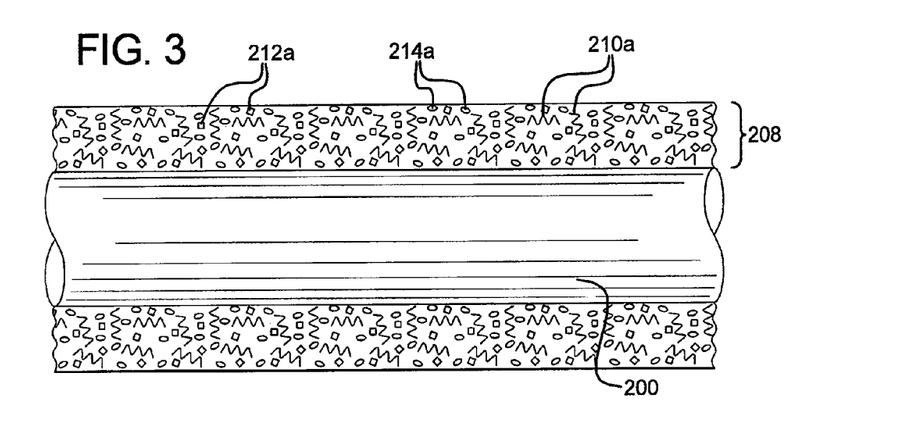
FIG. 3 is a side view, partially in section, of the medical device of FIG. 2 including an uncured coating applied to the surface thereof.

After preparing the medical wire for coating, a coating is applied to one or more surfaces of the medical wire as indicated in block 102 of FIG. 1. Referring to FIG. 3, the coating 208 includes a binder 210a, such as an epoxy, phenolic, phenoxy, polyimide, polyamide, polyamide-amide, polyphenylene sulfide, polyarylsulfone, polyethylene, polytetrafluoroethylene, fluorinated ethylene propylene, perfluoroalkoxy or any suitable binder or resin. Such suitable binders include any binder which, when cured, adheres to the surface of the medical device, and is flexible, stable, resistant to chemicals, and/or is readily sterilized and resistant to contamination. In one embodiment, the coating includes an ultraviolet light cure resin to semi or fully cure the coating. In another embodiment, the coating includes an electron beam cure resin.

The coating also includes at least one pigment 212a such as any suitable organic pigment, inorganic pigment, extender pigment, magnetic receptive pigment and/or laser excitable pigments. The organic pigments (with low to moderate heat resistance and which are represented as bright colors) include, but are not limited to, phthalocyanine blues and greens, diarylide yellows and oranges, quanacridone, naphthol and toluidine reds, carbizole violets, and carbon black. The inorganic pigments (with moderate to high temperature resistance and which are represented as dull to moderately bright colors) include, but are not limited to, iron oxide reds and yellows, chrome oxide greens, titanium oxide white, cadmium reds, ultramarine blues, moly oranges, lead chromate yellows, and mixed metal oxides of various shades of brown, yellow, blue, green and black. The extender pigments (which are inorganic and provide a reinforcing/strengthening function) include, but are not limited to, talc, calcium carbonate, silicate and sulfate, silica, mica, aluminum hydrate and silicate, and barium sulfate (blanc fixe/barites). The laser exciteable pigments (which are excited by laser energy), such as near-infrared reflective pigments include, but are not limited to, mica, pearl pigment, Kaolin and aluminum silicate derivatives, antomony trioxide, metallic pigment, aluminum flake pigment, and iron oxide. Additionally, the coating may also include one or more of the following functional pigments, such as conductive pigments, flatting pigments for controlling gloss, clays and other rheology modifying pigments.

In one embodiment, a coating which is formulated with magnetic receptive pigments and/or electromagnetic receptive pigments is utilized, wherein these magnetic receptive pigments will provide internal heat when subjected to one or more appropriate magnetic fields or electromagnetic fields. In this embodiment, such magnetic receptive pigments are applied to non-magnetic substrates, such as non-magnetic stainless steel, ceramics, plastic or polymers. Such magnetic receptive pigments are formulated with low-friction materials and appropriate color pigments and binders, such as epoxy and polyimide, which when cured at a suitable temperature provides adhesion to the substrate and also creates the low-friction surface. In this embodiment, the medical device is subsequently internally heated by exciting or energizing the dispersed magnetic receptive particles, which causes select areas of the medical device to change colors from the primary color to a darker color in the areas where the coated device is selectively subjected to the magnetic forces, while not overheating either the binder resin or the outer layer of low-friction material.

The pigment is configured to change color when heated above a color shifting temperature. The color shifting temperature is greater than, such as by 50-100° F. (10-38° C.), the designated temperature at which the coating is cured to allow the coating to be cured without changing the color of the pigment during the curing process. The color shifting temperature of the heat activated pigment should also be lower than the temperatures at which either the low-friction characteristics of the low-friction material, or the adhesive characteristics of the binder resin, are substantially affected, degraded, or deteriorated, or the chemical composition, characteristics, functions, or properties of the low-friction coating and/or base resin are changed.

The coating also includes particles of a low-friction material 214a such as PTFE. After curing, the low-friction material forms an at least partially transparent top coat such that at least some visible light passes through the low-friction material. In one embodiment, the particles are micron- and/or sub-micron-sized. In another embodiment, the low-friction material is resistant to chemicals such that the low-friction material will provide a low surface energy outer layer and not corrode, oxidize, break down, form bonds with other materials, or otherwise be affected by contacting other chemicals. In another embodiment, the low-friction material is pure and free of contaminants such that the low-friction material can safely be used in medical procedures and can safely contact food for human consumption. In another embodiment, the low-friction material is irradiated, prior to incorporation in the coating, with electron beam particles to create an easily wetted surface which enables better adhesion to the binder material.

In another embodiment, the coating includes additives, such as silane coupling agents, other materials formulated to improve the bonding capabilities of a coating to the surface of the medical wire, particularly smooth surfaces, or other materials which modify the curing characteristics or the drying characteristics of the coating before curing. In another embodiment, the coating includes additives to improve the wear characteristics, corrosion resistance, and/or electrical properties of the coating. For example, in one embodiment, the uncured coating includes approximately 30%-50% by volume of a base resin, 1%-30% of a heat stable pigment, and 0.5%-15% of a pigment that shifts from a first color to a second, contrasting color when heated from a first temperature to a second temperature which is 20-200° F. (11-93° C.) higher than the first temperature. The uncured coating also includes 2%-10% by volume of low-friction particles and trace amounts of a wetting agent, a silane coupling agent, a hardening agent, and/or curing or drying agents.

In one embodiment, a coating is applied by spraying the surface of a medical wire with the coating. In one embodiment, the coating is sprayed on by a siphon, gravity, or pressure pot method which forces the coating through a nozzle at high pressure such that the coating forms a vapor or mist which is directed toward the surface of the medical wire. In another embodiment, the coating is applied with a variation of siphon or gravity spraying wherein the coating is sprayed at a lower pressure and in higher volume to reduce the amount of volatile organic compounds released during the spraying process. In another embodiment, a medical wire device is dipped into a reservoir filled with the coating. Once submerged, the medical device or wire is removed from the reservoir and "spun" or rapidly rotated to remove excess coating by centrifugal force. In another embodiment, a medical device or wire is "tumbled" in a rotating barrel or other rotating enclosure including a coating. Hot air is blown over the tumbling medical wire to at least partially cure the coating as it is applied to the medical wire. In another embodiment, high speed rollers are used to apply a film of coating to the surface of a medical wire. In another embodiment, a medical wire is passed under a falling curtain of the coating to coat the surface of the medical wire.

In another embodiment, a powder coating system is employed. This powder coating system includes a primer, where required, of a liquid that is preapplied and either cured to dry or remains wet prior to the application of a topcoat of a powder. In this embodiment, the powder may include a low-friction material such as PFA, FEP, PTFE, PE or appropriate low-friction particles or a combination of the above plus appropriate pigments similar to those described in the liquid-type coatings described above.

In another embodiment, an electrostatic, tribo-charged or opposite electrostatic charged spray or powder spray method is used to apply the coating to a medical wire. The electrostatically charged spray enables an operator to better control the application uniformity of the coating and thereby enhances the uniformity, density and application of the coating on the surface of the medical wire. It should be appreciated that the coating may have one or more characteristics altered to allow for more efficient electrostatic, tribo-charged or opposite electrostatic charged spray techniques to be used to apply the coating to a medical wire.

Moreover, the above-described "tribo-charge", or electrically charged as with conventional electrostatic application technique alters the edge coverage thickness of the applied coating based on any design requirements which require a more uniformly applied coating to all surfaces of the medical wire, whether the configuration has sharp or round edges. This technique results in greater coating transfer efficiency while also optimizing the different edge coverage thicknesses of the applied coating, whether the medical device is a medical wire, medical guide wire, catheter, needle, knife, cannula, probe, or other medical device.

Referring to FIG. 3, one embodiment of the medical wire is illustrated wherein the medical wire includes an uncured coating 210 applied to its surface. After the coating is applied to the surface of the medical wire, the coating is cured as indicated in block 104 of FIG. 1 to harden the coating and strengthen the bond between the coating and the medical wire, thereby curing the coating. The curing process is performed by heating the coating at a predetermined temperature or temperatures for a predetermined length or lengths of time, air-drying the coating at ambient temperature, or by utilizing any suitable internal or external curing process. It should be appreciated that curing may be accomplished by exposure to light from an infrared, visible, or ultraviolet light source.

Figure 4:
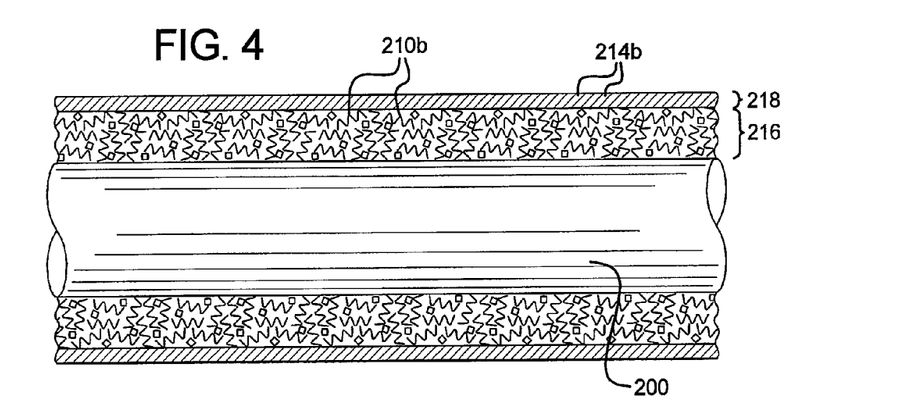
FIG. 4 is a side view, partially in section, of the medical device of FIG. 3 after the coating is cured.
Figure 5:
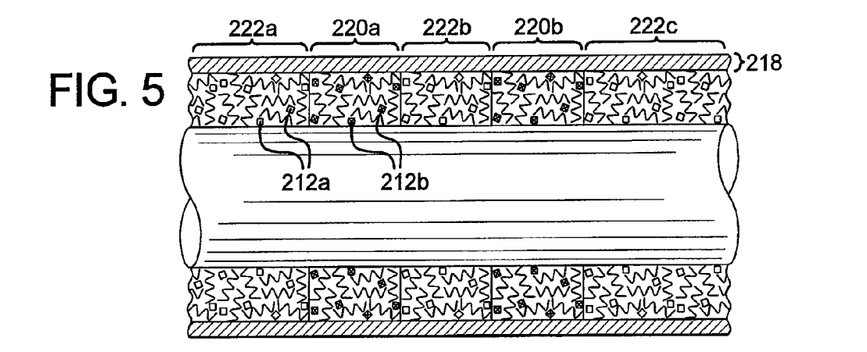
FIG. 5 is a side view, partially in section, of the coated medical device of FIG. 4 including markings resulting from shifting the color of selected areas of the base layer of the coating.

In one embodiment, as illustrated in FIG. 4, during the curing process, the molecules of a binder, such as an epoxy 210a crosslink and form chemical bonds with each other, and bond with the surface of the medical wire. The crosslinked epoxy molecules form an epoxy matrix 216 including crosslinked binder molecules, one or more low-friction materials, one or more pigments, and one or more other ingredients such as wetting agents, coupling agents, hardening agents, and/or other additives. Also during the curing process, the particles of low-friction material such as PTFE 214b soften and at least some of the PTFE or other low-friction material is squeezed out or displaced from the epoxy matrix and migrates, rises, or flows to the surface of the coating. At or near the surface of the coating, the PTFE molecules bond or fuse together to form a thin, partially transparent top coat 218 of PTFE on the outer surface of the coating. When the curing process is complete, as illustrated in FIG. 5, the coating includes a base layer including the epoxy matrix, and a top coat including fused molecules of PTFE. It should be appreciated that when the coating is cured, the epoxy matrix exhibits a first color, such as light blue, which is visible through the at least partially transparent PTFE top coat. Also, the surface of the coating 212 is smooth and resists sticking to other objects, which enables a surgeon or other medical professional to gently, smoothly, and accurately insert one end of the coated medical wire 220 into a patient's body.

Figure 6:
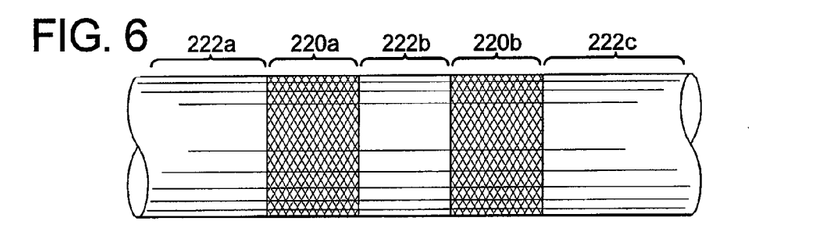
FIG. 6 is a side view of the coated medical device of FIG. 5.

Referring now to FIG. 5 and FIG. 6, in one embodiment, after curing the applied coating to harden the coating and form a low-friction top coat, markings 220a and 220b are created on the coated medical device or wire as indicated in Block 106 of FIG. 1. The markings are created by selectively heating portions of the coating above a color shifting temperature while simultaneously maintaining adjacent portions 222a, 220b, and 220c at a cooler temperature (with a suitable masking device). When heated above the color shifting temperature, the pigment in the selectively heated portions changes from a first color to a second color. For example, in one embodiment, as illustrated in FIG. 5, the coating applied to the medical wire is generally light blue in color. However, at measured intervals along the length of the medical wire, short sections of the base layer of the coating are dark brown or black in color. Thus, a first segment such as a 100 mm long segment of the coated medical wire is light blue in color. A second adjacent segment such as a 3 cm long segment of the coated medical wire is dark brown in color, and a third segment such as a 50 mm long segment, adjacent to the second segment, is light blue in color. The pattern of alternating light blue and dark brown or black segments is repeated from the proximal end to the distal end of the coated medical wire, resulting in a coated medical wire having markings which visually indicate each 50 mm of length of the coated medical wire. It should be appreciated that the color transitions of the coated medical device may be absolute (i.e., a first color ends and a second, contrasting color begins) or gradual or feathered (i.e., a first color bleeds into a second, transitioning color which bleeds into a third color which contrasts with the first color). The markings enable a surgeon or other medical professional to determine the length of the coated medical wire inserted into a patient's body (or the length of the coated medical wire remaining outside the patient's body) during a medical procedure.

Figure 7:
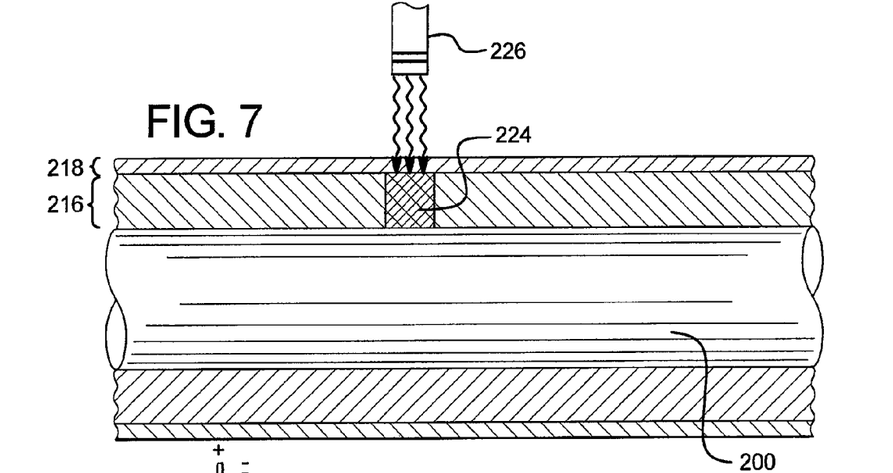
FIG. 7 is a side view, partially in section, of the coated medical device of FIGS. 5 to 6, including a laser for heating portions of the coating of the coated medical device.

Referring to FIG. 7, in one or more embodiments, the pigment in the coating is heated above the color shifting temperature by radiated heat. Radiated heat is applied from any radiant source, such as hot air, open flame, heated filaments, or lasers 226. Radiated heat can be directed to specific portions of the coating by masking portions of the coating (with a suitable masking device) that are not intended to be heated above the color shifting temperature. Masking is accomplished by any suitable mechanism configured to shield the coating from the heat source. In one embodiment, hot air is blown toward a specific portion of the coating through a nozzle or other apparatus of directing or funneling air. In another embodiment, When radiated or infrared heat is directed to a portion 224 of the coating, the at least partially transparent top coat allows certain designated amounts of radiated or infrared heat to pass through the top coat to the base layer, which absorbs the heat. This method heats the base layer while simultaneously keeping the low-friction top coat at a slightly cooler temperature, which has the advantage of preserving the low-friction character of the top coat and maintains the at least partial transparency of the top coat.

Figure 8:
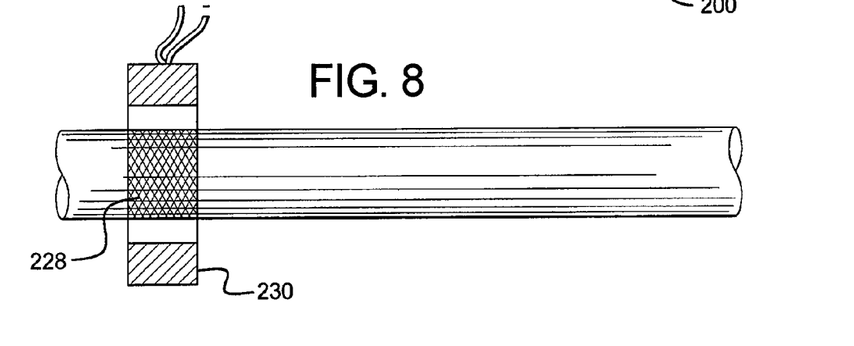
FIG. 8 is a side view of the coated medical device of FIGS. 5 to 6 including a magnetic induction coil for heating portions of the coated medical device.

Referring to FIG. 8, in one embodiment, the medical wire, which in this case is formed from a magnetic-type steel, is heated by magnetic induction wherein an induction coil 230 is energized with a frequency current, which imparts thermal energy in the medical wire. Electrical resistance in the medical wire causes electrical current energy to transform into heat energy. Heat from the medical wire then transfers to the base layer by thermal conduction, thus shifting the color of the portion of the base layer 228 above the heated segment of the medical wire. This method also has the advantage of keeping the low-friction top coat at a slightly cooler temperature, which preserves the low-friction character of the top coat. It should be appreciated that any suitable external energy source, such as flame heat, short wave infrared, medium wave infrared, hot air (electrically heated) with little orifices to make a small mark on the medical wire, induction heat provided through a "bobby pin" or circular shaped coil and/or at right angles, and/or heat provided using induction energy may be used to stimulate the pigment and/or binder resin to cause the pigment and/or binder resin to be heated to shift color.

In different embodiments, radiation, microwaves, concentrated sound waves or other vibrations, or other external energy sources may also be used to selectively stimulate the pigment and/or binder resin to cause the pigment and/or binder resin to shift color. In another embodiment, laser energy, such as provided by a $CO_2$ (carbon dioxide), YAG lasers (Ytterbium), and fiber laser systems, provide the necessary energy to selectively stimulate the pigment and/or binder resin to cause the pigment, additive and/or binder resin to shift color. In this embodiment, these lasers have different depths of penetration, different "dot" sizes and/or different energy outputs which can be pulsed to selectively stimulate the pigment and/or binder resin to cause the pigment and/or binder resin to shift color.

In one embodiment, the medical device disclosed herein is coated, cured and selectively heated in sequential order. For example, a 180 mm long medical wire is entirely coated, entirely cured and then selectively heated exactly in the center to a width of 5 cm to cause the pigment and/or binder resin to shift color. In another embodiment, different portions of the medical device are coated, cured and selectively heated simultaneously. For example, a first 1 foot portion of a 5 foot long medical wire is coated, while a second, different 1 foot portion of the 5 foot long medical wire is cured, while a third, different 1 foot portion of the 5 foot medical wire is selectively heated to cause the pigment and/or binder resin to shift colors. In these embodiments, the medical device is coated in a suitable coater or utilizing a suitable coating device, the medical device is cured in a suitable curer or utilizing a suitable curing device and the medical device is selectively heated with a selective heater or utilizing a suitable selective heating device.

In one embodiment wherein the medical device is a medical guide wire generally having the shape of a coiled spring, after the guide wire is formed, segments of the guide wire are selectively heated to shift the color of the heat activated pigment. The method of marking helically wound medical guide wire disclosed herein has the advantage of creating permanent markings at measured intervals along the length of the medical guide wire without weakening the medical guide wire, without creating debris or the potential for debris that could get caught between the adjacent turns of the medical guide wire, and without removing the low-friction coating or adversely affecting the function of the low-friction coating.

In another embodiment, a plurality of pigments having different color shifting temperatures are included in the coating. By selectively heating portions of the coating above the color shifting temperature of a first pigment but below the color shifting temperature of a second pigment, the color of the coating can be changed from a first color to a second different color. By selectively heating portions of the coating above the color shifting temperature of the second pigment, the color of the coating can be changed from the first color to a third different color. In one embodiment, for example, a coated medical wire includes a base color such as light blue, length markings in a second color, such as tan, and a second set of markings, such as a company logo, specifications, or use instructions in a third color such as brown or a lighter color such as white or tan.

In one embodiment, markings are created in the coating in any desired pattern or colors, or any combination of patterns and colors. In one such embodiment, the size of the markings and/or the number of marks grouped together to form a marking indicate different lengths of the marked medical device. In another such embodiment, small markings can be created at measured intervals along the length of the coated medical wire to indicate uniform lengths of the coated medical wire.

Figure 9:
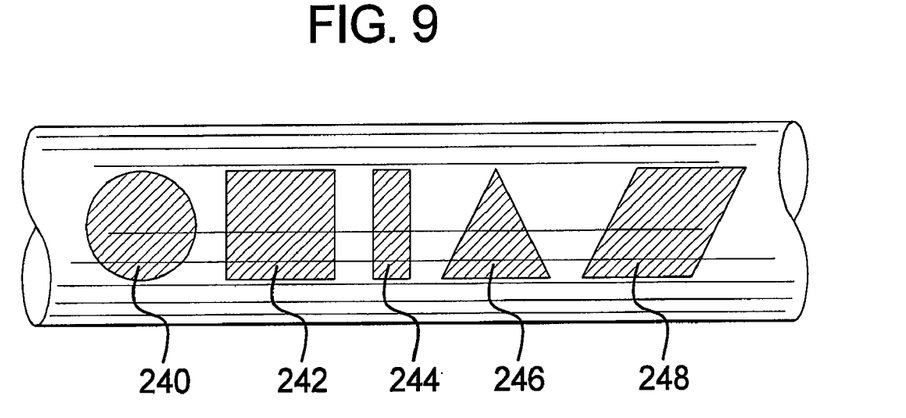
FIG. 9 is a side view of the coated medical device of FIGS. 5 to 6 including markings having geometric shapes.

In another embodiment, markings are created to indicate a specific distance from a reference point on the coated medical wire, such as a distance from the middle point, the proximal end and/or the distal end. For instance, one band having a shifted color can indicate a first distance from the distal end, while two bands having shifted colors in close proximity can indicate a second distance from the distal end. Likewise, in another embodiment, depending on the size and shape of the medical device, numbers or characters are created in the coating to indicate a distance from a middle point, the distal end and/or the proximal end. In another embodiment, as illustrated in FIG. 9, one or more geometric shapes, including but not limited to circles 240, squares 242, rectangles 244, triangles 246, parallelograms 248, and other polygrams are created in the coating to indicate lengths of the medical device.

Figure 10:
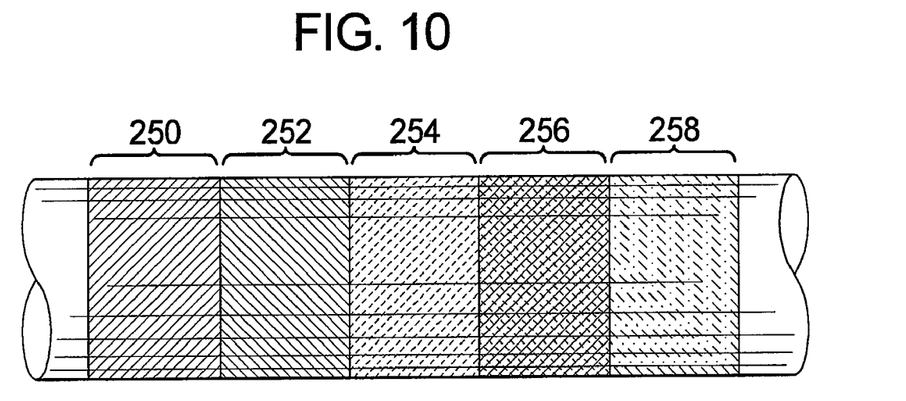
FIG. 10 is a side view of the coated medical device of FIGS. 5 to 6 including markings having different colors.

In another embodiment, a plurality of different colors are created to indicate distances from the middle point, proximal end or distal end of the medical device. The different colors are created by selectively heating a plurality of different pigments (with different properties and color shifting temperatures) above their respective color shifting temperatures. For example, in one embodiment, a progression of a plurality of uninterrupted colors is created along the length of the medical device. For illustrative purposes only, FIG. 10 illustrates one embodiment wherein a first 30 mm segment 250 of the coating of the medical wire is a first color. A second 30 mm segment 252 of the medical wire adjacent to the first segment is a second color. The adjacent segments 254, 256, and 258, each 30 mm long, are also each different colors. It should be further appreciated that a combination of one or more marking methods disclosed herein can provide a surgeon or other medical professional with additional information about the medical device. For example, the embodiment of FIG. 10 includes segments of different colors and also includes equally spaced markings of a first color, wherein the markings each indicate 10 mm of length.

Figure 11:
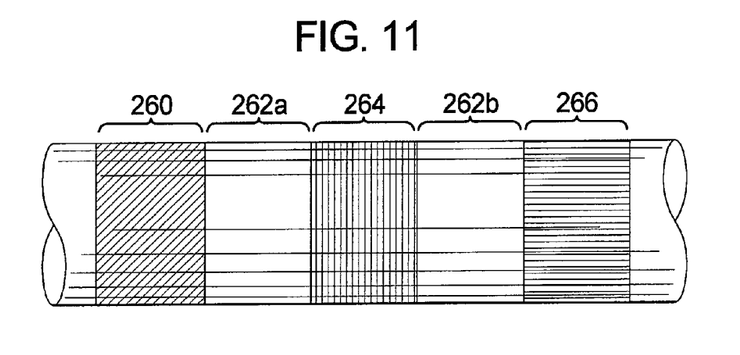
FIG. 11 is a side view of the coated medical device of FIGS. 5 to 6 including a progression of a plurality of interrupted colors along the length of the medical device.

In another embodiment, a progression of a plurality of interrupted colors is created along the length of the medical device. For illustrative purposes only, FIG. 11 illustrates one embodiment wherein a first segment 260 of the coating of the medical wire is a first color, a second segment 262a of the medical wire adjacent to the first segment has not been selectively heated and is a default, second color of the cured base material. For this example, a third segment 264 of the coating of the medical wire is a third color, a fourth segment 262b of the medical wire adjacent to the third segment has not been selectively heated and is the default, second color of the cured base material and a fifth segment 266 of the coating of the medical wire is a fourth color.

Figure 12:
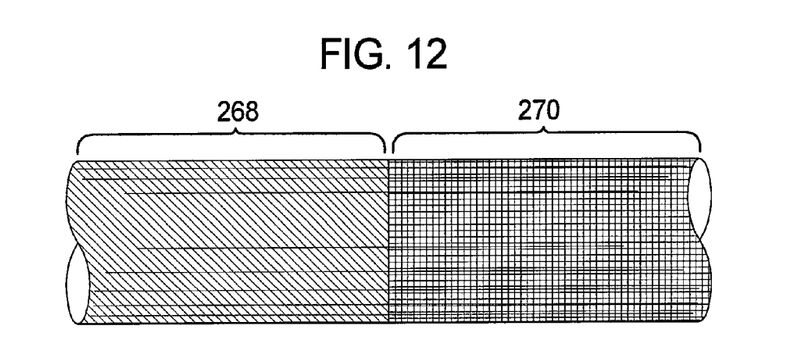
FIG. 12 is a side view of the coated medical device of FIGS. 5 to 6 including a first shifted color which runs from a distal end of the medical device to a halfway or middle point of the medical device and a second, different, contrasting color which runs from the proximal end of the medical device to the halfway or middle point of the medical device.

In another embodiment, a medical device disclosed herein includes a first shifted color (which runs from a distal end of the medical device to a halfway or middle point of the medical device) and a second, different, contrasting color (which runs from the proximal end of the medical device to the halfway or middle point of the medical device). For illustrative purposes only, FIG. 12 illustrates one embodiment wherein a first segment 268 of the medical wire (which runs from the distal end of the medical wire to a middle point) is coated and selectively heated to a first color shifting temperature to change the color of a first pigment (and thus change the color of the first segment) to a first color, such a green. As further seen in FIG. 12, a second segment 270 of the medical wire (which is of equal or substantially equal length as the first segment and runs from the proximal end of the medical wire to the middle point) is coated and selectively heated to a second color shifting temperature to change the color of a second, different pigment (and thus change the color of the second segment) to a second, different color, such as yellow. Such a configuration provides that a surgeon or medical professional can quickly identify when more than 50% of the medical device is internal to the patient and determine whether a different medical device of a different length should be employed. That is, the medical device of this embodiment (and other disclosed embodiments wherein different segments of a medical device are marked with different colors) is utilized by a surgeon or medical professional during a medical procedure to determine the length of the medical device inserted into a patient's body (i.e., by observing the color of the segments of the medical device that are external to the patient's body).

Figure 13:
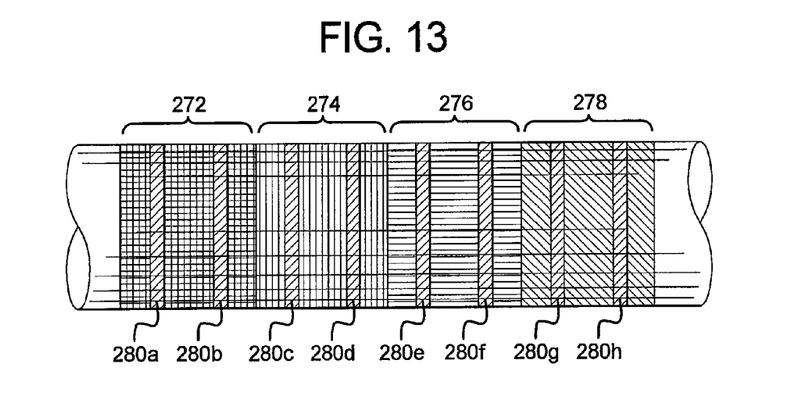
FIG. 13 is a side view of the coated medical device of FIGS. 5 to 6 including a plurality of pigments having different color shifting characteristics, wherein certain portions of the coating include a plurality of pigments that shift color.

In another embodiment, a plurality of pigments having different color shifting characteristics are included in the coating, wherein certain portions of the coating include a plurality of pigments that shift color. For illustrative purposes only, FIG. 13 illustrates one embodiment wherein a first segment 272 of the medical wire (which accounts for 25% of the length of the medical wire) is coated and selectively heated to a first color shifting temperature to change the color of a first pigment (and thus change the color of the first segment) to a first color, such as yellow. As further seen in FIG. 13, a second segment 274 of the medical wire (which accounts for another 25% of the length of the medical wire) is coated and selectively heated to a second color shifting temperature to change the color of a second pigment (and thus change the color of the second segment) to a second color, a third segment 276 of the medical wire (which accounts for another 25% of the length of the medical wire) is coated and selectively heated to a third color shifting temperature to change the color of a third pigment (and thus change the color of the third segment) to a third color and a fourth segment 278 of the medical wire (which accounts for another 25% of the length of the medical wire) is coated and selectively heated to a fourth color shifting temperature to change the color of a fourth pigment (and thus change the color of the fourth segment) to a fourth color. In this example, in addition to using heat activated pigments to shift the colors of the four segments, additional markings 280a to 280h are created along the length of the medical wire by utilizing laser activated pigments to selectively change certain portions of the medical wire a fifth color. That is, although one or more pigments located in the coating of the first segment of the medical wire were previously heat activated to change the first segment to a yellow color, additional pigments located in the coating of the first segment are laser activated to indicated marks 280a and 280b as a brown color in the first segment. Such a configuration provides that a surgeon or medical professional could utilize not only the color of the different segments of the medical device (i.e., to determine the length of the medical device inserted into a patient's body by observing the color of the segments of the medical device that are external to the patient's body) but could also count the number of marks for a segment that is partially internal and partial external to the patient's body to determine the exact length of the medical device utilized.

In another such embodiment which utilizes a plurality of pigments having different color shifting characteristics in the coating (not shown), a first segment of a coated medical device (which runs from the distal end of the medical wire to a middle point of the medical device) is selectively heated to a first color shifting temperature to change the color of a first pigment (and thus change the color of the first segment) to a first color, such a black. In this embodiment, a second segment of the medical device (which runs from the proximal end of the medical wire to the middle point) is then selectively heated to a second color shifting temperature to change the color of a second, different pigment (and thus change the color of the second segment) to a second, different color, such as yellow. In this embodiment, a third pigment located in certain portions of the first segment of the medical device are excited or otherwise activated to change to a third color, such as white (and thus create suitable markings in the first segment of the medical device) and a fourth pigment located in certain portions of the second segment of the medical device are excited or otherwise activated to change to a fourth color, such as brown (and thus create suitable markings in the second segment of the medical device).

It should be appreciated that the markings disclosed herein are not limited to indicating lengths, but also can indicate the size, type, material, part number, serial number, or manufacturer of the coated medical wire or medical device. The markings can also include bar codes or other codes, or other properties or instructions associated with the coated medical wire or medical device.

In another embodiment, different heat activated pigments are utilized to denote different lengths and/or sizes of different medical devices. For example, a first medical device of a first length is heated at or above a first color shifting temperature to cause a first pigment (in the base layer applied to the first medical device) to change to a first designated color. In this example, a second medical device of a second, different length is heated at or above a second color shifting temperature to cause a second pigment (in the base layer applied to the second medical device) to change to a second designated color. Accordingly, by utilizing different heat activated pigments, different medical devices of different lengths can be properly identified without increasing or decreasing the diameter of the medical device, or significantly adversely affecting the function of the low-friction coating applied to such medical devices.

In one embodiment, a plurality of anti-microbial particles such as silver, ceramic, silver ceramic, silver oxide, glass silver or silver compounds or any suitable anti-microbial agent are applied to one or more of the surfaces of the coated medical wire to reduce and kill bacteria and other potential germs that are located on the surface(s) of the coated medical wire or otherwise incorporated into the coating formulation. In one embodiment, the anti-microbial particles are interspersed with the uncured coating. During the curing process, some of the anti-microbial particles migrate or rise to the surface of the coating in addition to the low-friction material. The anti-microbial particles are capable of killing bacteria and other harmful organisms which contact the surface of the coated medical wire while in storage or while the medical device is deployed into the body. The coated medical wire therefore minimizes or reduces the chance of infections or other complications in the body after the surgical procedure is complete.

In another embodiment, one or more of the pigments in the coating are formulated to change or shift colors a plurality of times. For example, a designated pigment in the coating is initially a green or blue color that will change or shift to a white or white/grey color with one level of laser energy. In this example, the designated pigment will further change or shift to a dark black color with another, higher laser energy. Accordingly, such pigments are formulated, depending on the different levels of applied laser energy, different laser types or different color shifting temperatures, to provide a plurality of different color markings on a single medical device.

In another embodiment, a radiopaque material, such as barium sulfide, is added to the coating. In this embodiment, a suitable marking is provided or shows up an x-ray or x-ray device providing an exact location of the measurement inside a patient.

In another embodiment, a clear or transparent top coat is applied to one or more of the surfaces of the coated medical device after the visible marks are created in the base coating. In one embodiment, the top coating is a low-friction or release coating or material, such as fluorinated materials, polytetrafluoroethylene, perfluoro-alkoxy, fluoroethylenepropylene, MFA, polyethylene, silicone, ceramic composites, paralyene silane polymers and other suitable low-friction coatings. Such a top coating provides that the markings described above are substantially covered or sealed underneath an additional layer skin of a low friction coating. It should be appreciated that this additional layer is applied in a separate operation either after the color shift marks are created or after the marks are created in the base coat. In another embodiment, an ultraviolet cure ("uv cure") low-friction, thin layer of a special, clear, unpigmented, uv cure resin/fluoropolymer or resin/polyethylene material is formed over the marked medical device after the base coating is applied, cured and post marked. This lowers the friction of the surface since no heat is used to cure the uv material and no change in the marked lower base coating takes place which may be employed for lower temperature base materials like plastics or high friction reinforced plastics.

In another embodiment, a steel medical wire is treated with an iron, zinc, or manganese phosphate, which penetrates the steel surface and coats the surface of the medical wire with a thin layer of the phosphate, which promotes the adhesion of a coating, improves corrosion resistance, and improves the chemical protection of the medical wire. In another embodiment, conversion coating or anodizing of an aluminum medical wire is employed to promote adhesion of a coating to the medical wire and increase the surface hardness and corrosion resistance of the medical wire.

In another embodiment, at designated points on the medical device, the color shifting material is applied and the marks are created in a gradation of successively, incrementally darker colors by using gradually increasing or higher energy levels in directly adjacent areas to create a progressively darker and darker mark to further enhance the ability of the device manufacturer to create distance codes or even directional force guides on the medical device. This gradation of color shift method can be combined with cessation of energy input to create "breaks" in the color gradation to denote distance marks which are of the original color and are notably different from the gradation of darker markings.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of manufacturing a coated medical device, said method comprising:
    (a) applying a coating to at least a portion of a surface of a medical device, said coating including:
        (i) a binder;
        (ii) a pigment; and
        (iii) a plurality of low-friction particles of a low-friction material;
    (b) curing said applied coating at a designated cure temperature, said curing causing:
        (i) the binder to form a binder matrix adjacent to the surface of the medical device, said binder matrix including said pigment, and
        (ii) said plurality of low-friction particles to form an at least partially transparent top coat above said binder matrix including said pigment; and
    (c) selectively heating a designated quantity of portions of the cured coating such that said pigment of each selectively heated portion of the cured coating is heated above a color shifting temperature to cause said pigment to change from a first color to a second different color without changing functionality of said low-friction material of each selectively heated portion of the cured coating.

2. The method of claim 1, wherein the curing causes the low-friction particles to migrate from a first position below the pigment in the coating to a second position above the pigment in the coating.

3. The method of claim 1, wherein the pigment of each selectively heated portion of the cured coating is heated by an energy source selected from the group consisting of: a radiant heat, hot air, open flame, at least one electric filament, at least one magnet, and at least one laser.

4. The method of claim 1, wherein the pigment of each selectively heated portion of the cured coating is heated by conduction from the medical device, wherein said medical device is heated by induction.

5. The method of claim 1, wherein the coating includes a plurality of anti-microbial particles interspersed in said coating.

6. The method of claim 5, wherein the anti-microbial particles include at least one of the group consisting of silver particles, glass-silver particles, silver-ceramic particles and ceramic particles.

7. The method of claim 1, wherein the designated quantity of portions of the cured coating is one.

8. The method of claim 1, wherein the medical device is selected from the group consisting of: a medical wire, a medical guide wire, a catheter, a needle, a biopsy device, a cannula, a probe, and a blade.

9. The method of claim 1, wherein the binder is selected from the group consisting of: an epoxy, a phenoxy, a phenolic, a polyimide, a polyamide, a polyamide-amide, a polyarylsulfone, and a polyphenylene sulfide.

10. The method of claim 1, wherein the low-friction material is selected from the group consisting of: a polytetrafluoroethylene, a fluorinated ethylene propylene, a perfluoroalkoxy, a polyethylene, a silicone, a modified fluoropolymer, an irradiated polymer powder, and an irradiated polymer particle.

11. The method of claim 1, wherein the pigment is selected from a group consisting of: a phthalocyanine blue, a phthalocyanine green, a diarylide yellow, a diarylide orange, a quanacridone, a naphthol, a toluidine red, a carbazole violet, a carbon black, an iron oxide red, an iron oxide yellow, a chrome oxide green, a titanium oxide white, a cadmium red, a ultramarine blue, a moly orange, a lead chromate yellow, a mixed metal oxide, a talc, a calcium carbonate, a silicate and sulfate, a silica, a mica, an aluminum hydrate and silicate, a barium sulfate, a pearl pigment, a kaolin, an aluminum silicate derivative, an antimony trioxide, a metallic pigment, an aluminum flake pigment, and an iron oxide.

12. The method of claim 1, wherein the pigment is selected from a group consisting of a heat activated pigment, an organic pigment, an inorganic pigment, an extender pigment, a magnetic receptive pigment, and a laser excitable pigment.

13. A method of manufacturing a coated medical device, said method comprising:
   (a) applying a coating to at least a portion of a surface of a medical device, said coating including:
      (i) a binder;
      (ii) a plurality of pigments including at least a first pigment configured to change from a first color to a second color when heated above a first color shifting temperature, and a second pigment configured to change from a third color to a fourth color when heated above a second different color shifting temperature; and
      (iii) a plurality of low-friction particles of a low-friction material;
   (b) curing said applied coating at a designated cure temperature, said curing causing:
      (i) the binder to form a binder matrix adjacent to the surface of the medical device, said binder matrix including said plurality of pigments, and
      (ii) said plurality of low-friction particles to form an at least partially transparent top coat above said binder matrix including said plurality of pigments;
   (c) selectively heating at least a first portion of said cured coating above the first color shifting temperature to cause the first pigment of the first portion of said cured coating to change from the first color to the second color without changing functionality of said low-friction material of the first portion of said cured coating; and
   (d) selectively heating at least a second portion of said cured coating above the second color shifting temperature to cause the second pigment of the second portion of said cured coating to change from the third color to the fourth color without changing functionality of said low-friction material of the second portion of said cured coating.

14. The method of claim 13, wherein the first color and the third color are different.

15. The method of claim 13, wherein the second color and the fourth color are different.

16. The method of claim 13, wherein the first portion of said cured coating is adjacent to the second portion of said cured coating.

17. The method of claim 13, wherein the size of the first portion of the cured coating indicates a measurement of distance.

18. The method of claim 13, which includes applying an ultra-violet cured fluoropolymer layer to at least one of the selectively heated portions of the cured coating.

19. The method of claim 13, which includes applying a release coating to at least one of the selectively heated portions of the cured coating.

20. The method of claim 13, wherein the curing of said coating causes the low-friction particles to migrate from a first position below the pigment in the coating to a second position above the pigment in the coating.

21. The method of claim 13, wherein the first pigment of the first portion of said cured coating is heated by an energy source selected from the group consisting of: a radiant heat, hot air, open flame, at least one electric filament, at least one magnet and at least one laser.

22. The method of claim 13, wherein the first pigment of the first portion of said cured coating is heated by conduction from the medical device, wherein said medical device is heated by induction.

23. The method of claim 13, wherein the coating includes a plurality of anti-microbial particles interspersed in said coating.

24. The method of claim 23, wherein the anti-microbial particles include at least one of the group consisting of silver particles, glass-silver particles, silver-ceramic particles and ceramic particles.

25. The method of claim 13, wherein (c) is repeated for a plurality of first portions of the cured coating.

26. The method of claim 13, wherein the medical device is selected from the group consisting of: a medical wire, a medical guide wire, a catheter, a needle, a biopsy device, a cannula, a probe, and a blade.

27. The method of claim 13, wherein the binder is selected from the group consisting of: an epoxy, a phenoxy, a phenolic, a polyimide, a polyamide, a polyamide-amide, a polyarylsulfone, and a polyphenylene sulfide.

28. The method of claim 13, wherein the low-friction material is selected from the group consisting of: a polytetrafluoroethylene, a fluorinated ethylene propylene, a perfluoroalkoxy, a polyethylene, a silicone, a modified fluoropolymer, an irradiated polymer powder, and an irradiated polymer particle.

29. The method of claim 13, wherein the first pigment is selected from a group consisting of: a phthalocyanine blue, a phthalocyanine green, a diarylide yellow, a diarylide orange, a quanacridone, a naphthol, a toluidine red, a carbizole violet, a carbon black, an iron oxide red, an iron oxide yellow, a chrome oxide green, a titanium oxide white, a cadmium red, a ultramarine blue, a moly orange, a lead chromate yellow, a mixed metal oxide, a talc, a calcium carbonate, a silicate and sulfate, a silica, a mica, an aluminum hydrate and silicate, a barium sulfate, a pearl pigment, a kaolin, an aluminum silicate derivative, an antimony trioxide, a metallic pigment, an aluminum flake pigment, and an iron oxide.

30. The method of claim 13, wherein the second pigment is selected from a group consisting of: a phthalocyanine blue, a phthalocyanine green, a diarylide yellow, a diarylide orange, a quanacridone, a naphthol, a toluidine red, a carbizole violet, a carbon black, an iron oxide red, an iron oxide yellow, a chrome oxide green, a titanium oxide white, a cadmium red, a ultramarine blue, a moly orange, a lead chromate yellow, a mixed metal oxide, a talc, a calcium carbonate, a silicate and sulfate, a silica, a mica, an aluminum hydrate and silicate, a barium sulfate, a pearl pigment, a kaolin, an aluminum silicate derivative, an antimony trioxide, a metallic pigment, an aluminum flake pigment, and an iron oxide.

31. The method of claim 13, wherein the first pigment is selected from a group consisting of a heat activated pigment, an organic pigment, an inorganic pigment, an extender pigment, a magnetic receptive pigment, and a laser excitable pigment.

32. The method of claim 13, wherein the second pigment is selected from a group consisting of a heat activated pigment, an organic pigment, an inorganic pigment, an extender pigment, a magnetic receptive pigment, and a laser excitable pigment.

* * * * *